United States Patent [19]

Perraudin et al.

[11] 4,362,947

[45] Dec. 7, 1982

[54] IRRADIATION APPARATUS USING RADIOACTIVE SOURCES

[75] Inventors: Claude Perraudin, Meudon; Edmond Amargé, Pringy; Jean P. Guiho, Le Mesnil St. Denis; Jean C. Horiot, St. Jullien; Gérard Taniel, Les Essarts Le Roi; Georges Viel; Jean P. Brethon, both of Orsay, all of France

[73] Assignee: C.G.R.-MeV, Commissariat a l'Energie Atomique, Paris, France

[21] Appl. No.: 223,725

[22] Filed: Jan. 9, 1981

[30] Foreign Application Priority Data

Jan. 11, 1980 [FR] France ................. 80 00614

[51] Int. Cl.³ .................. G21F 3/02; G21K 1/04
[52] U.S. Cl. ................................. 378/150
[58] Field of Search ............. 250/510, 512, 513, 514, 250/505, 503

[56] References Cited

U.S. PATENT DOCUMENTS

| | | |
|---|---|---|
| 2,542,196 | 2/1951 | Haupt . |
| 2,667,588 | 1/1954 | Oswald ................. 250/513 |
| 2,722,611 | 11/1955 | Haput . |
| 3,091,696 | 5/1963 | Peyser ................. 250/513 |
| 3,539,813 | 11/1970 | Resnick ................. 250/513 |
| 4,034,288 | 7/1977 | Arauner ................. 250/511 |
| 4,128,767 | 12/1978 | Stödberg et al. ......... 250/513 |

Primary Examiner—Bruce C. Anderson
Attorney, Agent, or Firm—Cushman, Darby & Cushman

[57] ABSTRACT

An irradiation apparatus for obtaining an irradiation beam having precise and easily adjustable dimensions. This apparatus comprises more particularly a secondary collimation device having an axis Y—Y, removably fixed to the mobile arm of the irradiation apparatus and comprising a conical pot, two pairs of frames which support collimating plates and are movable about shafts fixed to said conical pot, each of said frames being connected to said conical pot by means of a compass system formed from legs hinged together about shafts. With said frames are associated mobile antipenumbra plates whose position is checked by means of a feeler system.

6 Claims, 5 Drawing Figures

ID RADIATION APPARATUS USING
RADIOACTIVE SOURCES

BACKGROUND OF THE INVENTION

The present invention relates to an irradiation apparatus using radioactive sources such as cobalt 60 for example and more particularly a secondary collimation device for delivering an irradiation beam of precise, easily-adjustable dimensions eliminating the penumbral areas.

SUMMARY OF THE INVENTION

It is an object of the invention to provide an irradiation apparatus using at least one radioactive source comprising a fixed support with which is associated an arm movable about an axis X—X, an irradiation head comprising an enclosure made from a material impermeable to the radiation of the source and, in this enclosure, a first biological protection screen surrounding at least partially a second biological protection screen, this second screen having a housing for receiving the radioactive source, a primary collimator for collimating the radiation emitted by the radioactive source and a secondary system for collimating the beam comprising a conical pot made from a material impermeable to the irradiation beam and, integral with this conical pot, two pairs of frames, each of the frames, movable about a rotational shaft fixed to the conical pot, being associated with a mechanical moving system, each frame being provided with collimating plates disposed substantially perpendicularly to this frame, each frame of the secondary collimation device being connected to the conical pot through a compass system formed from two legs hinged to each other about an axis dd, one of the legs being rotatable about a shaft bb fixed to the conical pot and the other leg being rotatable about a shaft cc fixed to the frame considered, the shafts dd, bb, cc being parallel to the axis of rotation of the frame on which the compass system is fixed.

DESCRIPTION OF THE DRAWINGS

The invention will be better understood and other characteristics will appear from the following description and accompanying drawings in which:

FIG. 5 shows a system for eliminating the penumbra associated with a frame of the secondary collimator.

DESCRIPTION OF THE PREFERRED EMBODIMENT

Figure 1:
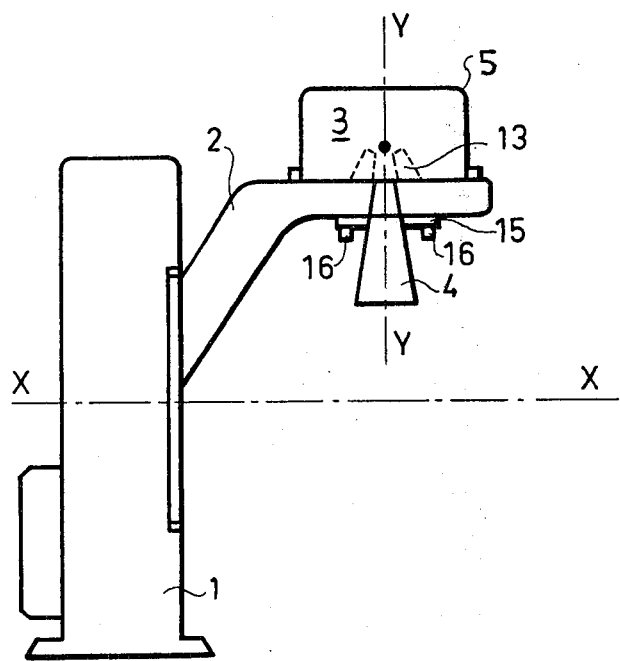
FIG. 1 shows schematically an irradiation apparatus in accordance with the invention.

The irradiation apparatus shown in FIG. 1 and which may be used advantageously in radiotherapy comprises:
 a fixed support 1;
 an arm 2 movable about an axis X—X;
 an irradiation head 3;
 a primary collimator 13;
 a secondary collimation device 4 having axis Y—Y perpendicular to the axis X—X.

Figure 2:
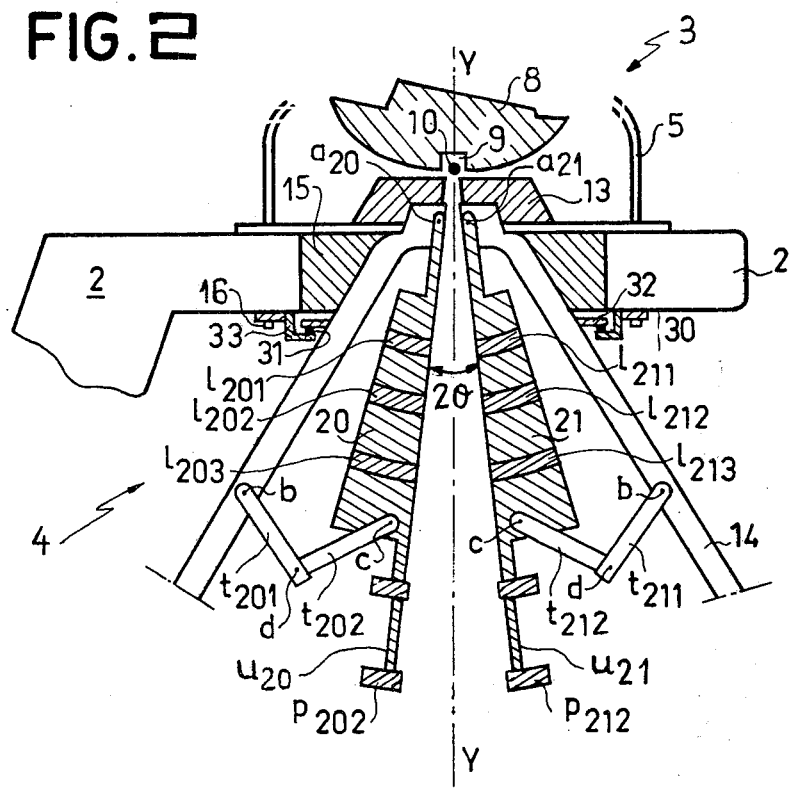
FIG. 2 shows, in longitudinal section, a secondary collimation system used in the irradiation apparatus of the invention.

Irradiation head 3 comprises, in a way known per se, an enclosure 5 in which are placed a first fixed biological protection screen, not visible in FIG. 2, surrounding at least partially a second mobile biological protection screen 8, this second screen 8 having a housing 9 for receiving a radioactive source 10. This housing 9 opens outwardly of screen 8 so as to let pass therethrough the irradiation beam delivered by radioactive source 10.

An optical simulation system of known type, enabling the irradiation beam to be simulated and allowing the suitably positioning of the zone to be irradiated, may be associated with the irradiation head 3.

The irradiation apparatus of the invention has a primary collimator 13 with axis Y—Y, of a known type, and a secondary collimation device 4 in accordance with the invention. This secondary collimation device 4, removably fixed to mobile arm 2 by means of a support plate 15 for example and screws 16, is described hereafter.

This secondary collimation device (FIG. 2) comprises a conical pot 14 made from a material impermeable to the radiation of radioactive source 10, two pairs of frames 20, 21; 22, 23 (only frames 20, 21 can be seen in FIG. 2) integral with conical pot 14. Frames 20, 21 comprise respectively a series of plates $l_{201}$, $l_{202}$, $l_{203}$ and $l_{211}$, $l_{212}$, $l_{213}$; . . . disposed one after another and perpendicular to the frame with which they are associated.

Frames 20, 21, movable respectively about axes $a_{20}$ and $a_{21}$ fixed to the conical pot 14 are associated with a mechanical moving system allowing them to move simultaneously and in an identical fashion. The same goes for two other frames disposed in a plane perpendicular to the plane formed by frames 20, 21. These other frames (not visible in FIG. 2) are mobile about axes identical to those of frames 20, 21, and another mechanical moving system, identical to the one mentioned above, is associated with these two other frames.

Figure 4:
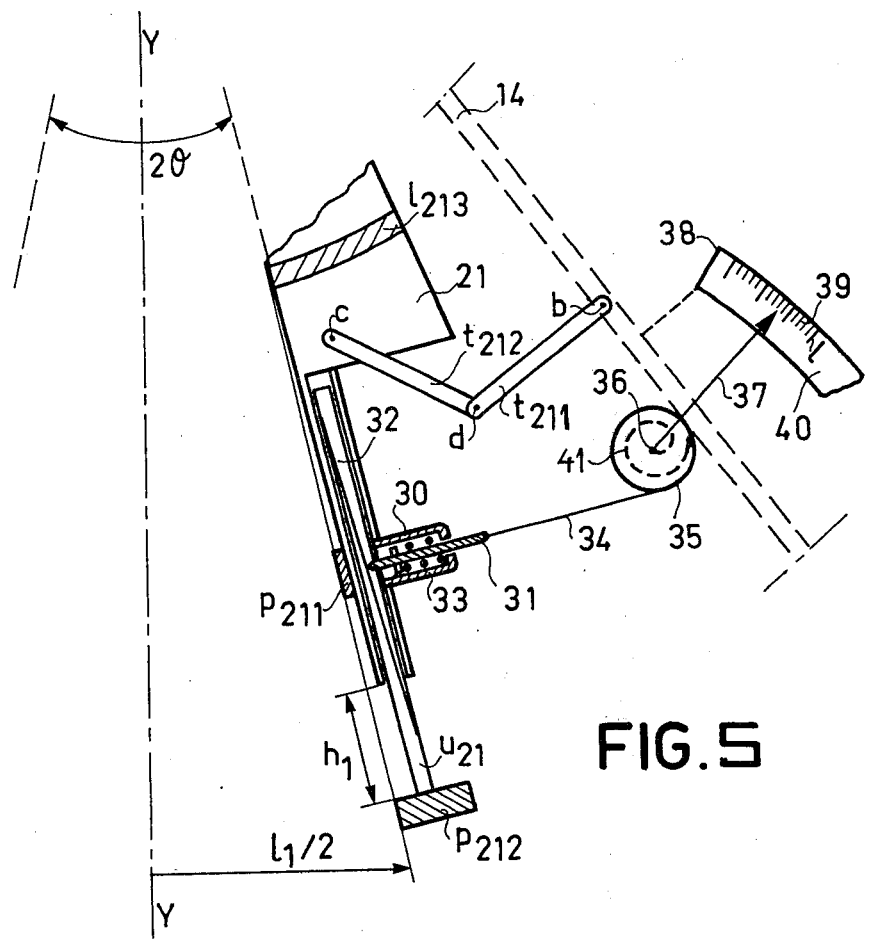
FIG. 4 shows a system for moving the frames of the secondary collimator.
Figure 4:
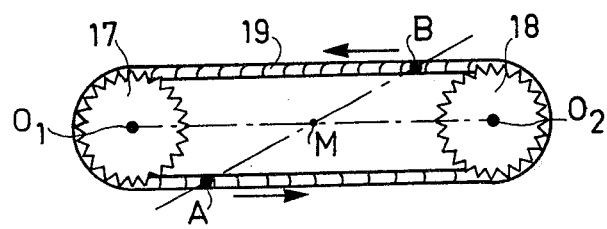

FIG. 4 shows schematically, by way of nonlimiting example, a mechanical system for moving frames 20, 21 placed facing each other. This system comprises two change-of-direction pinions 17, 18 rotatable about shafts passing through their respective centers $O_1$, $O_2$ and a chain 19 passing over these pinions 17, 18. Frames 20, 21 are fitted respectively to chain 19 at points A and B symmetrical with respect to a point M situated midway between centers $O_1$, $O_2$. These points A and B and so frames 20, 21 move in opposite directions when the system is put into operation.

Figure 3:
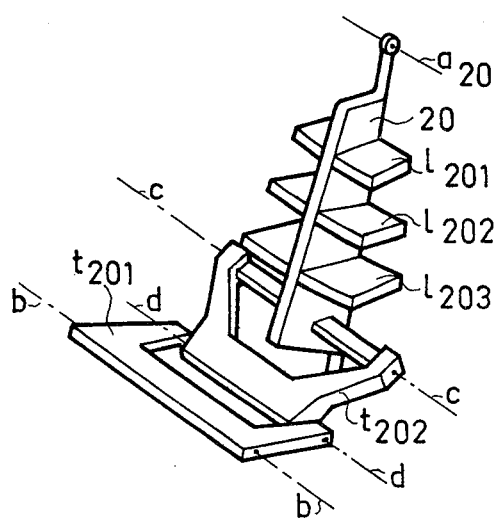
FIG. 3 shows a partial view, in perspective, of the collimation system of FIG. 2.

So as to avoid any play prejudicial to the proper operation of the collimation device each of these frames 20, 21 . . . of the secondary collimation device of the invention, is associated with a compass system shown in detail in FIG. 3. The compass system associated with frame 20 comprises a first leg $t_{201}$ movable about a shaft bb fixed to the conical pot 14, a second leg $t_{202}$ movable about a shaft cc perpendicular to frame 20 and fixed to this frame 20. Legs $t_{201}$ and $t_{202}$ are hinged to each other about a free shaft dd. The only movements of legs $t_{201}$, $t_{202}$ are then rotational movements about shafts bb, cc, dd so that frames 20, 21 rest coplanar during their movement.

Point screws may ensure the final positioning of legs $t_{201}$, $t_{202}$.

Also in accordance with the invention, the secondary collimation device has a system for eliminating penumbra.

In fact, when radioactive source 10 has a large diameter (1 to 2 cm for example) the edges of the treatment field are affected by a penumbra, resulting from the geometrical form of the secondary collimation device, the two facing frames 20 and 21 being movable about two shafts $a_{20}$ and $a_{21}$ separated from one another by a distance greater than the diameter of radioactive source 10.

FIG. 5 shows a detail of this penumbra elimination system where only frame 21 has been shown. With this frame 21 are associated two penumbra elimination plates $P_{211}$, $P_{212}$. Plate $P_{212}$ is fixed to the end of a rod $u_{21}$ slidably mounted in the corresponding frame 21. Plate $P_{211}$ is fixed to frame 21. The opening angle $2\theta$ of facing frames 20, 21 and the position of mobile plate $P_{212}$ are verified by means of a position-checking system associated with each pair of frames 20, 21 (and 22, 23). To each opening angle $2\theta$ of the associated frames there corresponds a position of facing plates $P_{202}$ and $P_{212}$ (only plate $P_{212}$ can be seen in FIG. 5) for eliminating the penumbra at the edges of the treatment field. As shown in FIG. 5, the system for checking the opening angle $2\theta$ and the position of plate $P_{212}$ comprises a case 30 fixed to frame 21. Inside this case 30 there is placed a feeler 31 which is applied, by means of a spring 33, against the bottom of a groove 32 provided in rod $u_{21}$ and being slidable in frame 21. This groove 32 is oblique with respect to the sliding axis. At the free end of feeler 31 there is fixed one of the ends of a thread 34, the other end of thread 34 being fixed to the periphery of a drum 35 circular in section rotatable about a shaft 36 passing through its center and fixed to conical pot 14. A needle 37 integral with drum 35 can move over a graduated scale 38 placed inside conical pot 14.

In the embodiment shown in FIG. 5 fixed penumbra plate $P_{211}$ is integral with case 30.

A return spring 41 is placed in drum 35 so as to maintain thread 34 tensioned. This spring 41 is fixed, on the one hand, to shaft 36 and, on the other hand, to durm 35.

In operation, to a given value of the opening angle $2\theta$ of frames 20 and 21 and a given position of penumbra elimination plates $P_{202}$ and $P_{212}$ (distance between plates $P_{202}$, $P_{212}$ equal to $h_1$) there corresponds a width $l=l_1$ of the treatment field (the value of l is indicated on the graduated scale 38). For the same opening angle $2\theta$ and another position of plates $P_{201}$, $P_{212}$, the width l of the treatment field is equal to $l_2$. Scale 38, associated with a pair of frames 20, 21 for example, supplies then one of the dimensions (the width l) of the treatment field, rectangular in shape for example. The other dimension will be supplied by an identical control system, associated with the other pair of frames (not shown).

In the embodiment described, penumbra elimination plates $P_{202}$, $P_{212}$ placed facing each other may be positioned simultaneously, in an identical way, either manually, or for example by means of a motor coupled to rods $u_{20}$, $u_{21}$ supporting respectively plates $P_{202}$, $P_{212}$.

In another embodiment, a system for checking the dimensions of the treatment field may be associated with each of frames 20, 21 . . . the graduated scales 38 associated with these frames 20, 21 . . . then giving respectively the values of distances $d_1$, $d_2$ separating two of the edges of the treatment field at axis Y—Y. (In this case we must have $d_1=d_2=\frac{l}{2}$).

Further, in the embodiment shown in FIG. 2 of the secondary collimation device of the invention, the conical pot 14 may rotate about axis Y—Y. In fact, a system 30 for securing this conical pot 14 to the mobile arm 2 comprises a bearing 31 inserted between two bearing blocks 32, 33, bearing block 32 being integral with conical pot 14 and bearing block 33 removably fixed to mobile arm 2.

What is claimed is:

1. An irradiation apparatus using at least one radioactive source and comprising a fixed support with which there is associated an arm movble about an axis X—X, an irradiation head comprising an enclosure made from a material impermeable to the radiation of the source and, in said enclosure, a first biological protection screen surrounding at least partially a second biological protection screen, said second screen having a housing for receiving the radioactive source, a primary collimator and a secondary collimation device comprising a conical pot made from a material impermeable to the irradiation beam and, integral with said conical pot with axis Y—Y, two pairs of frames, each of the frames, movable about a shaft fixed to said conical pot, being associated with a mechanical moving system, each frame having collimating plates disposed substantially perpendicularly to the frame on which they are fixed, each frame of the secondary collimation device is connected to the conical pot by means of a compass system formed from two legs hinged together about a shaft dd, one of the legs being rotatable about a shaft bb fixed to the conical pot and the other leg being rotatable about a shaft cc fixed to the frame considered, said shafts being parallel to the axis of rotation of the frame on which is fixed the compass system.

2. An irradiation apparatus as claimed in claim 1, wherein this mechanical system for moving two frames placed facing each other comprises two change-of-direction pinions rotatable about shafts passing through their center and a chain surrounding the pinions, said frames being fixed respectively to said chain at two points symmetrical with respect to a point situated midway between said centers.

3. An irradiation apparatus as claimed in claim 1, wherein the secondary collimation device is provided with a penumbra elimination system comprising, associated with each frame, a plate fixed on a rod which may slide respectively in the corresponding frame and wherein control systems for determining the opening angle of the facing frames as well as the position of the penumbra elimination plates are associated with pairs of frames.

4. An irradiation apparatus as claimed in claim 3, wherein the system for checking the position of the frames and of the corresponding penumbra elimination plates comprises, associated with at least one pair of facing frames, a case fixed on the frame, there being fixed in this case a feeler penetrating into a groove, oblique with respect to the sliding axis, of a rod sliding in the frame, a spring for applying this feeler to the bottom of the oblique groove, wherein, at the free end of the feeler there is fixed one of the ends of a thread, the other end of said thread being fixed to the periphery of a circular drum rotatable about an axis passing through its center, and wherein a needle is fixed to the drum, perpendicularly to the axis, this needle being movable over a graduated scale.

5. An irradiaton apparatus as claimed in claim 3, wherein said conical pot is integral with a support plate intended to be fixed by means of screws to said mobile arm.

6. An irradiation apparatus as claimed in claim 5, wherein said conical pot is associated with a fixing system for fixing it removably to said mobile arm, said fixing system comprising a plate disposed perpendicularly to axis Y—Y and forming a bearing block integral with said conical pot, a bearing block removably fixed to said mobile arm and, between said bearing blocks, a bearing.

* * * * *